United States Patent
Lai et al.

(10) Patent No.: US 11,633,620 B2
(45) Date of Patent: Apr. 25, 2023

(54) METHOD AND SYSTEM FOR OPTOGENETICS EXPERIMENTS

(71) Applicant: The Hong Kong Polytechnic University Shenzhen Research Institute, Shenzhen (CN)

(72) Inventors: Puxiang Lai, Shenzhen (CN); Lei Sun, Shenzhen (CN); Tianting Zhong, Shenzhen (CN); Zhihai Qiu, Shenzhen (CN)

(73) Assignee: THE HONG KONG POLYTECHNIC UNIVERSITY SHENZHEN RESEARCH INSTITUTE, Shenzhen (CN)

( * ) Notice: Subject to any disclaimer, the term of this patent is extended or adjusted under 35 U.S.C. 154(b) by 336 days.

(21) Appl. No.: 16/843,674

(22) Filed: Apr. 8, 2020

(65) Prior Publication Data

US 2021/0154489 A1 May 27, 2021

(30) Foreign Application Priority Data

Nov. 27, 2019 (CN) .......................... 201911184827.1

(51) Int. Cl.
*A61N 5/06* (2006.01)
*A61K 48/00* (2006.01)

(52) U.S. Cl.
CPC ........ *A61N 5/0601* (2013.01); *A61K 48/0083* (2013.01); *A61N 5/062* (2013.01); *A61N 2005/063* (2013.01); *A61N 2005/0629* (2013.01)

(58) Field of Classification Search
CPC .................. A61N 5/0601; A61N 5/062; A61N 2005/0629; A61N 2005/063; A61N 5/067;
(Continued)

(56) References Cited

U.S. PATENT DOCUMENTS

2005/0070987 A1  3/2005 Erickson
2012/0123236 A1* 5/2012 Boulanot ............... A61B 90/11
                                                        600/378
(Continued)

FOREIGN PATENT DOCUMENTS

CN  101093360 A  12/2007
CN  102106722 A   6/2011
(Continued)

OTHER PUBLICATIONS

Chinese Office Action for Chinese Application No. 201911184827.1 dated May 30, 2022; 10 Pages.
(Continued)

*Primary Examiner* — Brian T Gedeon
*Assistant Examiner* — Joshua Andrew Schum-Houck
(74) *Attorney, Agent, or Firm* — Cantor Colburn LLP

(57) ABSTRACT

A method for optogenetics experiments, based on wavefront shaping and including: calculating the transmission matrix between an input end and an output end of the multimode fiber under a fixed shape; implanting the output end into an intracranial space of an experimental subject; and performing wavefront compensation to a light to be input into the input end, according to the spatial position of the optical stimulation and the transmission matrix of the multimode fiber, to form a compensated expanded light, and inputting the compensated expanded light from the input end into the multimode fiber, such that the compensated expanded light, after being transmitted by the multimode fiber to the output end and output from the output end, is capable of focusing at the spatial position of the optical stimulation.

10 Claims, 5 Drawing Sheets

(58) Field of Classification Search
CPC ............. A61N 5/0622; A61K 48/0083; C12N 2740/10043; C12N 15/86; A01K 67/0275; A01K 2217/203; A61D 1/00
See application file for complete search history.

(56) References Cited

U.S. PATENT DOCUMENTS

| | | | |
|---|---|---|---|
| 2018/0228375 A1 | 8/2018 | Kim et al. | |
| 2018/0303573 A1* | 10/2018 | Trulson | ............... A61B 5/0071 |
| 2018/0369607 A1 | 12/2018 | Zhang et al. | |
| 2019/0168021 A1 | 6/2019 | Jackson et al. | |
| 2019/0227152 A1* | 7/2019 | Czarske | ................... G02B 6/04 |

FOREIGN PATENT DOCUMENTS

| | | | |
|---|---|---|---|
| CN | 106108858 | A | 11/2016 |
| CN | 107121772 | A | 9/2017 |
| CN | 206848565 | U | 1/2018 |
| CN | 206876950 | U | 1/2018 |
| CN | 109060124 | A | 12/2018 |
| CN | 109350087 | A | 2/2019 |
| EP | 3096171 | A1 | 11/2016 |
| JP | 2011128639 | A | 6/2011 |
| JP | 2019117684 | A | 7/2019 |
| WO | 2005093793 | A1 | 10/2005 |
| WO | 2018148767 | A1 | 8/2018 |

OTHER PUBLICATIONS

Machine Translation of Chinese Office Action for Chinese Application No. 201911184827.1 dated May 30, 2022; 6 Pages.

* cited by examiner

METHOD AND SYSTEM FOR OPTOGENETICS EXPERIMENTS

CROSS-REFERENCE TO RELATED APPLICATIONS

This application claims priority to Chinese Patent Application No. 201911184827.1 filed on Nov. 27, 2019, the contents of which are incorporated herein by reference.

BACKGROUND

Technical Field

The present application relates to the technical field of biomedical engineering, in particular to a method and a system for optogenetics experiments.

Description of Related Art

Karl Deisseroth's laboratory at Stanford University has announced that humans formally possessed optogenetics as a tool for precise brain manipulation, after expressing light sensitive proteins in neuronal cells and realizing the regulation of neural functions in response to light stimuli of different wavelengths. Optogenetics is a biomedical engineering science born in the 21st century and is currently in a period of rapid development. This field integrates multiple disciplines such as optics, biological gene manipulation technology, electrophysiology, and software programming. In the past, people's understanding of the interactions between neurons only stayed on the correlation. Fortunately, through optogenetics, people can explore the causal relationship between specific neural circuits and brain functions. This minimally invasive and accurate neurooperation technology, when using as a neuroscience research tool, is undoubtedly a great improvement.

Selective stimulation of neuronal cells with cellular resolution and high temporal resolution is a major goal in neuroscience. It will enable precise brain manipulation with specific time sequence to advance our understanding on how the human brain works and to treat diseases. Neurons can sense, transduce, and respond to various external stimuli such as electric, magnetic, heat, and mechanical stimuli. Although unmodified neurons may be stimulated directly to evoke action potentials with external techniques such as deep brain stimulation (DBS), such techniques lacked specificity and selectivity to individual neurons. Alternatively, with inserted well-characterized light sensitive proteins (e.g. opsins), the chosen neurons are enabled to respond to optical stimulation, while leaving other cells silent. The light can be delivered into deep tissue though a tiny optical fiber inserted into the specific region, which enables free moving animal manipulations in vivo. These kinds of technology have been used as a golden standard for dissecting brain circuits in the last few decades.

However, in the conventional technical scheme of optical stimulation to the neuronal cells, the light come out from the fiber is divergent and forming a light spot (single-mode fiber) or a speckle pattern (multimode fiber) that is much larger than the cell size. While in neural circuit controlling specific behaviors, the divergence of the neurons is spatiotemporal sequence coded, it is required to accurately stimulate the neurons in the subset of chosen neurons. In the meanwhile, the existing optical stimulation systems including the multi-photon scheme have an effective working range being greatly limited by the objective conditions, which can only realize optical stimulation within a few hundred micrometers beneath the brain surface. This is far from enough for optogenetics experiments in many scenarios. Therefore, optical stimulation of neurons with existing technologies cannot achieve precise stimulation in the ideal scenario of optogenetics.

SUMMARY

In view of the above-described problems, it is an object of the present application to provide a method for precise optogenetics experiments, which aims at solving the technical problem that the conventional method for optogenetics experiments has poor spatial selectivity and cannot realize precise stimulation to the chosen neuronal cells.

The present application is achieved as follows: a method for optogenetics experiments, based on wavefront shaping, comprises:

acquiring a transmission matrix, comprising: using a multimode fiber as a transmission fiber for optical stimulation signals, fixing a shape of the multimode fiber, and calculating the transmission matrix between an input end and an output end of the multimode fiber under the shape;

performing brain implant, comprising: implanting the output end into an intracranial space of an experimental subject, wherein the shape of the multimode fiber remains fixed before and after the brain implant; and providing an optical stimulation, comprising: enabling a spatial position of the optical stimulation to be within a field of view of the output end, performing wavefront compensation to a light to be input into the input end, according to the spatial position of the optical stimulation and the transmission matrix of the multimode fiber, to form a compensated expanded light, and inputting the compensated expanded light from the input end into the multimode fiber, such that the compensated expanded light, after being transmitted by the multimode fiber to the output end and output from the output end, is capable of focusing at the spatial position of the optical stimulation.

In an embodiment of the present application, in the step of acquiring a transmission matrix, said calculating the transmission matrix between an input end and an output end of the multimode fiber under the shape comprises:

collecting a light distribution information of a light field at the output end of the multimode fiber multiple times when a specific compensated expanded light is input into the input end of the multimode fiber; or alternatively, collecting a light distribution information of a light field at the input end of the multimode fiber multiple times when a specific compensated expanded light is input into the output end of the multimode fiber; and calculating the transmission matrix of the multimode fiber by using a transmission matrix solution algorithm according to the light distribution information collected multiple times.

In an embodiment of the present application, the light distribution information of the light field comprises: a light intensity and a light phase information of the light field.

In an embodiment of the present application, in the step of providing an optical stimulation, the compensated expanded light is modified according to an optical environment of the intracranial space of the experimental subject, and the compensated expanded light is capable of focusing at a predetermined spatial coordinate after the output end of the multimode fiber is implanted into the intracranial space of the experimental subject.

In an embodiment of the present application, the method further comprises, after the step of providing an optical stimulation, performing time sequence optical stimulation.

In an embodiment of the present application, the step of performing time sequence optical stimulation comprises:

performing time sequence variable wavefront compensation to the light to be input into the input end, according to a relation function between the spatial position of the optical stimulation and the time and the transmission matrix of the multimode fiber, to form a time sequence compensated expanded light; and inputting the time sequence compensated expanded light from the input end into the multimode fiber, such that the time sequence compensated expanded light, after transmitted by the multimode fiber to the output end and output from the output end, is capable of dynamically focusing within the field of view of the output end according to the relation function between the spatial position of the optical stimulation and the time.

In an embodiment of the present application, in the step of performing time sequence variable wavefront compensation to the light to be input into the input end of the multimode fiber to form the time sequence compensated expanded light, a digital micromirror device is adopted to perform spatial light modulation, wherein the compensated expanded light is output by the digital micromirror device, by continuously updating an output pattern of the digital micromirror device, the time sequence variable wavefront compensation is achieved and the time sequence compensated expanded light is formed.

In an embodiment of the present application, the method further comprises, before said performing the bran implant, transcribing a gene expressing light sensitive proteins into the intracranial space of the experimental subject.

In an embodiment of the present application, the step of transcribing a gene expressing light sensitive proteins into the intracranial space of the experimental subject comprises: injecting a retrovirus into the intracranial space of the experimental subject, wherein a gene of the retrovirus contains a gene segment capable of being expressed as the light sensitive proteins.

It is another object of the present application to provide a system for optogenetics experiments, adopting the above method for optogenetics experiment.

Advantages of the method for optogenetics experiments provided according to embodiments of the present application are summarized as follows:

The method for optogenetics experiments provided by embodiments of the present application adopts the wavefront shaping technology to perform phase compensation on an expanded light. In particular, by using the calculated transmission matrix of the multimode fiber and the spatial light modulation principle, after the spatial position of the optical stimulation point is determined, the wavefront of the expanded light entering into the input end are shaped for the phase compensation. Due that the shape of the multimode fiber is fixed, the transmission matrix is totally controlled with the shape thereof fixed and can be obtained from calculation. The compensated expanded light obtained from the wavefront shaping can focus at the pre-determined optical stimulation point after entering the input end and propagated via the multimode fiber. That is, the method for optogenetics experiments provided by embodiments of the present application can achieve precise optical stimulation within the field of view of the output end of the multimode fiber, which greatly increases the spatial selectivity of optical stimulation in optogenetics experiments to a single neuronal cell precision, thereby achieving precise optical stimulation to the specific neuronal cells.

BRIEF DESCRIPTION OF THE DRAWINGS

In order to more clearly illustrate the technical solutions in the embodiments of the present application, the drawings used in the embodiments or the prior art description will be briefly described hereinbelow. Obviously, the drawings in the following description are only some embodiments of the present application. Other drawings may be obtained from those skilled in the art without departing from the scope of the application.

Figure 1:
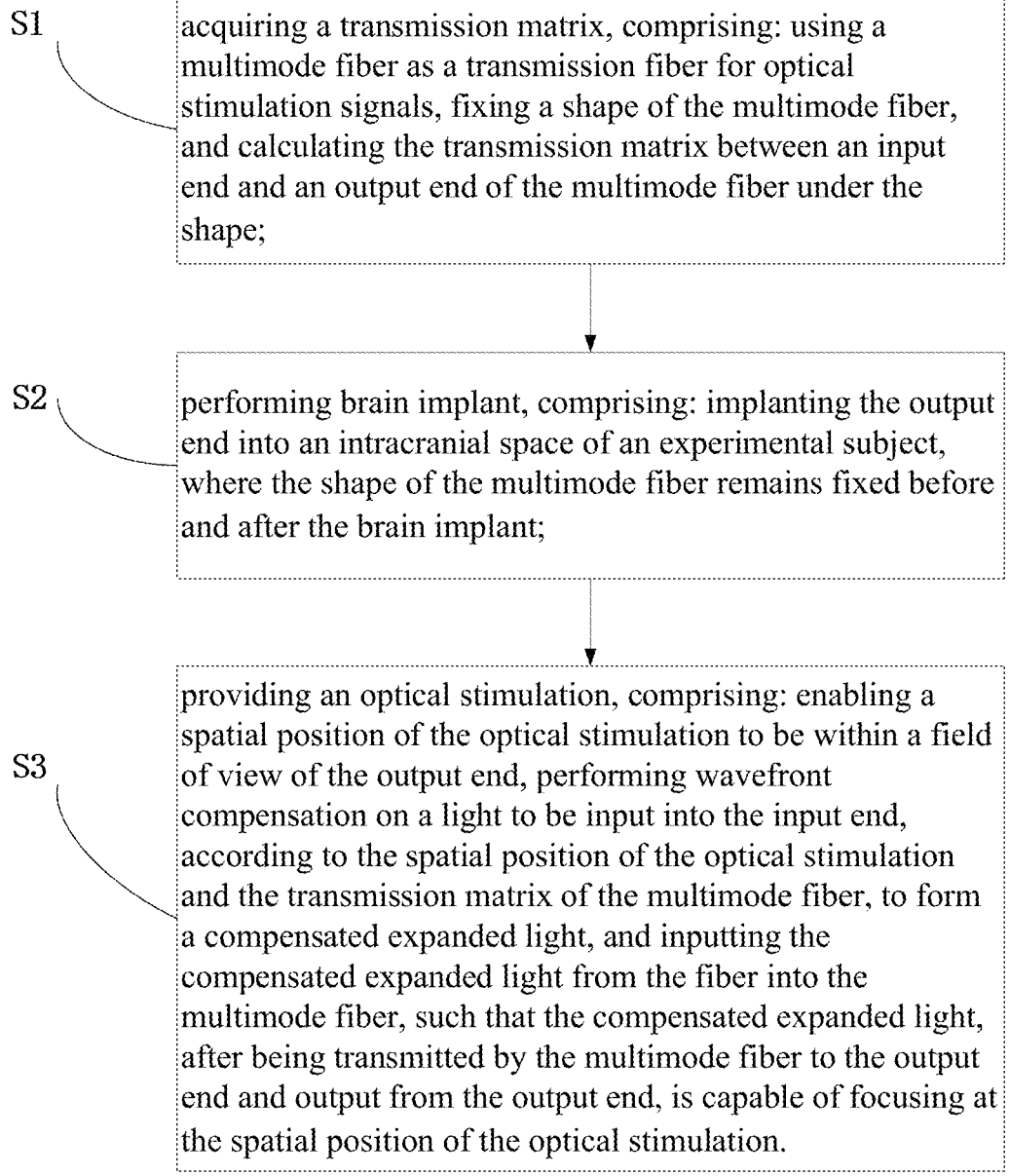
FIG. 1 is a flow chart of a method for optogenetics experiments in accordance with an embodiment of the present application.

1-Expanded light source; 2-Digital micromirror device; 3-Multimode fiber; 31-Input end; 32-Output end; and 4-Experimental subject.

DETAILED DESCRIPTION OF THE EMBODIMENTS

In order to make the purposes, technical solutions, and advantages of the present application clearer and more understandable, the present application will be further described in detail hereinafter with reference to the accompanying drawings and embodiments. It should be understood that the embodiments described herein are only intended to illustrate but not to limit the present application.

It should be noted that when an element is described as "fixed" or "arranged" on/at another element, it means that the element can be directly or indirectly fixed or arranged on/at another element. When an element is described as "connected" to/with another element, it means that the element can be directly or indirectly connected to/with another element. Terms like "length", "width", "upper", "lower", "front", "rear", "left", "right", "vertical", "horizontal", "top", "bottom", "inside", "outside" indicating orientation or positional relationship are based on the orientation or the positional relationship shown in the drawings, and are merely for facilitating and simplifying the description of the present application, and thus should not be construed as limiting the application. Terms like "first" and "second" are only used for the purpose of description, and will in no way be interpreted as indication or hint of relative importance or implicitly indicate the number of the referred technical features. Terms like "multiple"/"a plurality of" refer to the number of two or more than two, except for clear and particular restriction.

In order to explain the technical solutions of the present application, detailed description is given below with reference to specific drawings and embodiments.

Figure 5:
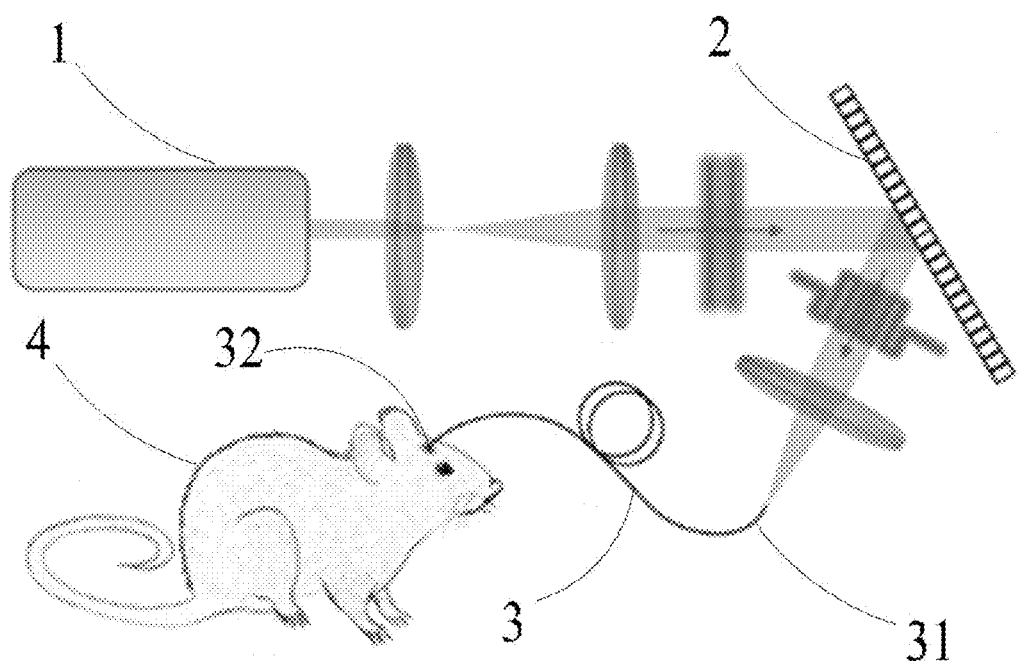
FIG. 5 is a schematic diagram of a system for optogenetics experiments in accordance with an embodiment of the present application The following reference numerals are adopted.

Referring to FIGS. 1 and 5, an embodiment of the present application provide a method for optogenetics experiments, and the method comprises the following steps:

S1: acquiring a transmission matrix, comprising: using a multimode fiber 3 as a transmission fiber for optical stimulation signals, fixing a shape of the multimode fiber 3, and calculating the transmission matrix between an input end 31 and an output end 32 of the multimode fiber 3 under the shape;

S2: performing brain implant, comprising: implanting the output end 32 into an intracranial space of an experimental subject 4, where the shape of the multimode fiber 3 remains fixed before and after the brain implant;

S3: providing an optical stimulation, comprising: enabling a spatial position of the optical stimulation to be within a field of view of the output end 32, performing wavefront compensation to a light to be input into the input end 31 by using a spatial light modulator, such as the digital micromirror device 2, according to the spatial position of the optical stimulation and the transmission matrix of the multimode fiber 3, to form a compensated expanded light, and inputting the compensated expanded light from the input end 31 into the multimode fiber 3, such that the compensated expanded light, after being transmitted by the multimode fiber 3 to the output end 32 and output from the output end 32, is capable of focusing at the spatial position of the optical stimulation.

The method for optogenetics experiments provided by embodiments of the present application adopts the wavefront shaping technology to perform phase compensation on an expanded light. In particular, by using the calculated transmission matrix of the multimode fiber 3 and the spatial light modulation principle, after the spatial position of the optical stimulation point is determined, the wavefront of the expanded light entering into the input end 31 are shaped for the phase compensation. Due that the shape of the multimode fiber is fixed, the transmission matrix is totally controlled with the shape thereof fixed and can be obtained from calculation. The compensated expanded light obtained from the wavefront shaping can focus at the pre-determined optical stimulation point after entering the input end 31 and propagated via the multimode fiber 3. That is, the method for optogenetics experiments provided by embodiments of the present application can achieve precise optical stimulation within the field of view of the output end 32 of the multimode fiber 3, which greatly increases the spatial selectivity of optical stimulation in optogenetics experiments to a single neuronal cell precision, thereby achieving precise optical stimulation to the specific neuronal cells.

In addition to the above advantages, the method for optogenetics experiments provided by embodiments of the present application at least has the following technical effects: because the multimode fiber 3 is implanted into the intracranial space of the experimental subject 4 for optical stimulation, the slender optical fiber can minimize the damage to the neuronal cells of the experimental subject 4. The optical fiber can be embedded into the deep brain of the experiment subject 4 for optical stimulation, which can not only minimize the damage to the neuronal cells of the experimental subjects, but also realize precise optical stimulation of the neuronal cells in the deep brain of the experimental subject 4. In the meanwhile, in condition that the optical stimulation point is located at the neuronal cells with a distance relatively far away from the output end 32, the intracranial tissue between the output end 32 and the target neuronal cells can be used as a part of the wavefront compensation content, that is, when calculating the transmission matrix, the light scattering and phase loss caused by the intracranial matter can be taken into account. In this way, the calculated transmission matrix calculated can greatly improve the optical stimulation depth of the compensated expanded light, and the effective optical stimulation can be achieved on those neuronal cells much further away from the output end 32.

As a preferred technical solution of this embodiment, the intensity of the compensated expanded light should satisfy two conditions. One is that the energy density of the light focusing at the optical stimulation point can reach a threshold value for activating the ion channels on the neuronal cells of the optical stimulation point. The other is that, when the light output from the output end 32 passes through other neuron cells in the intracranial space of the experimental subject 4, the ion channels on these neuronal cells will not be activated by the unfocused compensated expanded light. Such light intensity achieves optical simulation with cell scale precision, which avoids optical stimulation of insufficient intensity and prevents such optical stimulation with insufficient intensity from stimulating other neuronal cells on the optical stimulation path, such that the manipulation of activation or dormancy of specific neuronal cells can be achieved through optical stimulation.

As a specific technical solution of this embodiment, in step S2: when performing the brain implant, an auxiliary device such as a space locator can be used to place the output end in front of a target area to ensure that the output end can be accurately and stably implanted into a specific position in the intracranial space of the experimental subject 4.

In an embodiment of the present application, in the step of acquiring a transmission matrix, said calculating the transmission matrix between an input end 31 and an output end 32 of the multimode fiber 3 under the shape comprises: collecting a light distribution information of a light field at the output end 32 of the multimode fiber 3 multiple times when a specific compensated expanded light is input into the input end 31 of the multimode fiber 3; or alternatively, collecting a light distribution information of a light field at the input end 31 of the multimode fiber 3 multiple times when a specific compensated expanded light is input into the output end 32 of the multimode fiber 3; and calculating the transmission matrix of the multimode fiber 3 by using a transmission matrix solution algorithm according to the light distribution information collected multiple times.

Figure 2:
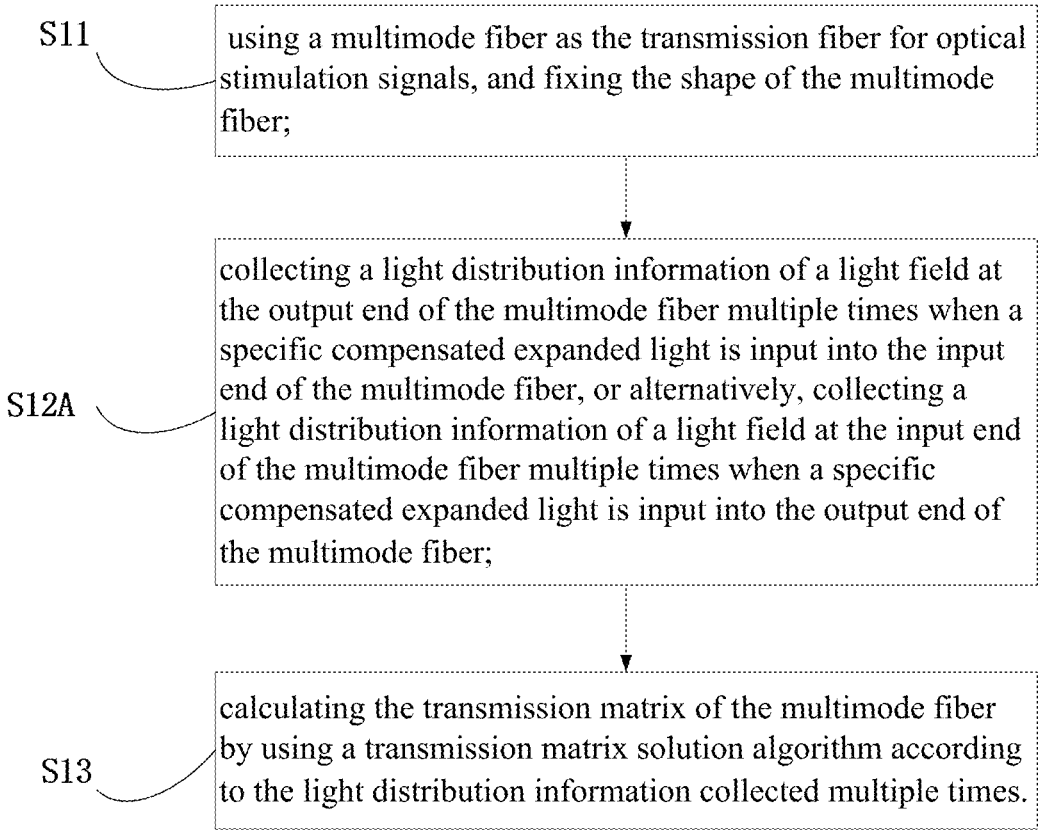
FIG. 2 is a flow chart of acquisition of a transmission matrix in accordance with an embodiment of the present application.

As shown in FIG. 2 and FIG. 5, the step of acquiring a transmission matrix specifically comprises:

S11: using a multimode fiber 3 as the transmission fiber for optical stimulation signals, and fixing the shape of the multimode fiber 3;

S12A: collecting a light distribution information of a light field at the output end 32 of the multimode fiber 3 multiple times when a specific compensated expanded light is input into the input end 31 of the multimode fiber 3; or alternatively, collecting a light distribution information of a light field at the input end 31 of the multimode fiber 3 multiple times when a specific compensated expanded light is input into the output end 32 of the multimode fiber 3; and S13: calculating the transmission matrix of the multimode fiber 3 by using a transmission matrix solution algorithm according to the light distribution information collected multiple times.

As a specific technical solution of this embodiment, a spatial light modulator, such as a digital micromirror device 2, can be used to continuously change the incident light at one end of the multimode fiber 3 according to the algorithm, while using a high speed camera to record light distribution information of the output light field at the other end. In this way, after a limited number of times transformations (the number of times is determined by the algorithm), the transmission matrix can be calculated according to the light distribution information of the light field after multiple transformations. Because the digital micromirror device 2 and the high speed camera are used for measurement, such operation can be completed in several minutes, which is beneficial to improve the efficiency of obtaining the transmission matrix.

The transmission matrix model of a strong scattering medium is very complicated and has a large amount of information. It is not necessary to completely solve the transmission matrix of the multimode fiber. Therefore, the method for optogenetics experiments provided by embodiments of the present application does not need a spatial optical phase modulator (slow speed) to solve the complete transmission matrix when calculating the transmission matrix, but only needs a binary spatial light modulator (DMD) for high-speed modulation. By collecting the light distribution information of a working plane of the output end 32 of the multimode fiber 3 multiple times, and combining with the modulation information corresponding to the input end 31 of the multimode fiber 3, an approximate solution of the transmission matrix can be calculated. According to the approximate solution, wavefront shaping of the compensated expanded light is achieved, and focused imaging at a specific position within the field of view of the output end 32 can be achieved. After the solution of the multimode fiber the transmission matrix is calculated, for focus at different target sites, no further optimization is required. Based on the transmission matrix, the compensation required for a specific site can be calculated; and the spatial light modulator to perform the compensation is used to perform the compensation, such that the focus can be achieved at the specific site, thereby greatly improving the use efficiency of the transmission matrix without losing the precision of the focus position.

In an embodiment of the present application, the light distribution information of the light field comprises: a light intensity and a light phase information of the light field.

Figure 3:
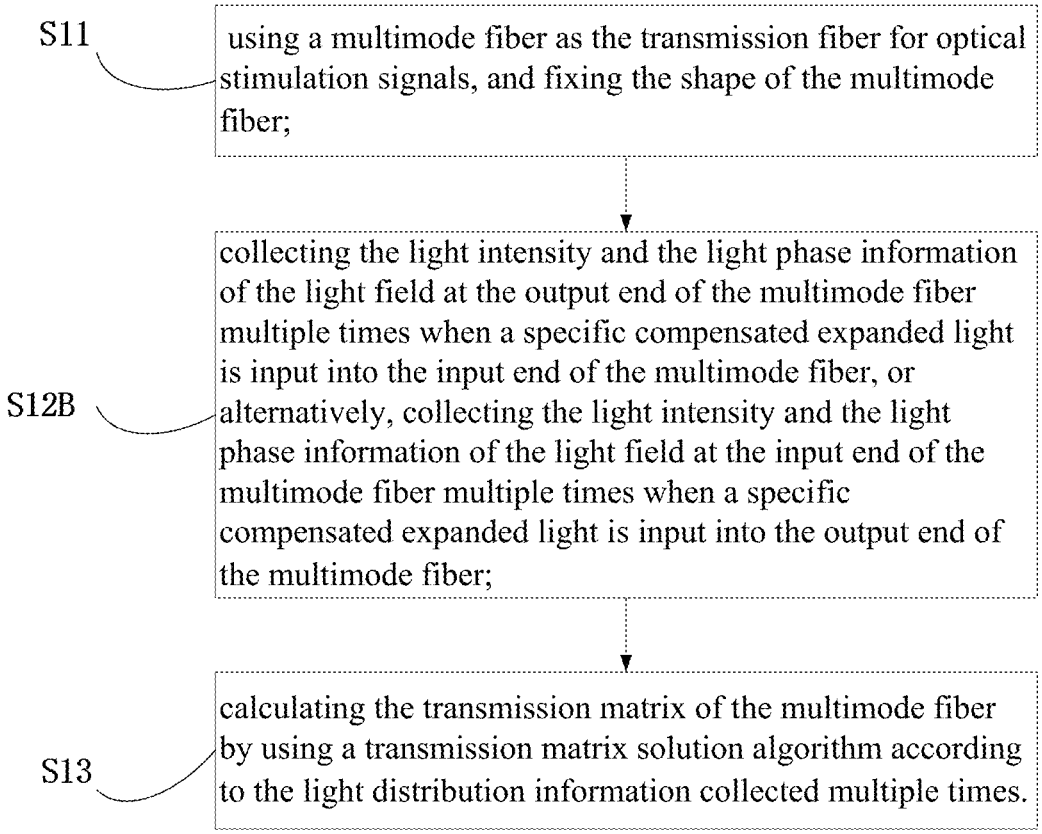
FIG. 3 is a flow chart of acquisition of a transmission matrix in accordance with another embodiment of the present application.

Referring to FIG. 3 and FIG. 5, the step of acquiring a transmission matrix specifically comprises:

S11: using a multimode fiber 3 as the transmission fiber for optical stimulation signals, and fixing the shape of the multimode fiber 3;

S12B: collecting the light intensity and the light phase information of the light field at the output end 32 of the multimode fiber 3 multiple times when a specific compensated expanded light is input into the input end 31 of the multimode fiber 3; or alternatively, collecting the light intensity and the light phase information of the light field at the input end 31 of the multimode fiber 3 multiple times when a specific compensated expanded light is input into the output end 32 of the multimode fiber 3; and S13: calculating the transmission matrix of the multimode fiber 3 by using a transmission matrix solution algorithm according to the light distribution information collected multiple times.

When the compensated expanded light is input to one end of the multimode fiber 3 through the digital micromirror device, the transmission matrix model is calculated based on the light intensity and the light phase information of the light field at the other end of the multimode fiber 3. Furthermore, according to the transmission matrix model, the spatial light modulator (SLM) is used to compensate the light intensity and the light phase of the compensated expanded light. The light focus at any specific spatial coordinate within the field rang of the output end 32 can be realized, thereby greatly improving the spatial precision of the optical stimulation.

In an embodiment of the present application, in the step of providing an optical stimulation, the compensated expanded light is modified according to an optical environment of the intracranial space of the experimental subject 4, such that the compensated expanded light is capable of focusing at a predetermined spatial coordinate after the output end 32 of the multimode fiber 3 is implanted into the intracranial space of the experimental subject 4.

In particular, the spatial position of the optical stimulation is located within the field of view of the output end 32. According to the spatial position of the optical stimulation, the transmission matrix of the multimode fiber 3, and the optical environment of the intracranial space of the experimental subject 4, the light to be input into the input end 31 of the multimode fiber 3 is performed with wavefront compensation by using the spatial light modulator, such as the digital micromirror device 2, so as to form the compensated expanded light. The compensated expanded light is input from the input end 31 into the multimode fiber 3, such that the compensated expanded light after being transmitted via the multimode fiber 3 to the output end 32 and output from the output end 32 can focus at the spatial position of the optical stimulation.

In the method for optogenetics experiments provided in this embodiment, since during its actual operation, the intracranial environment of the experimental subject 4 is very complicated and has a strong ability to scatter light with high scattering complexity. Based on the optical environment in the intracranial space of the experimental subject 4, compensation is performed in the process of inputting the wavefront shaping light into the input end 32, such that the precise focusing at multiple spatial coordinate positions within the filed range of the output end 32 of the multimode fiber can be achieved and the optical stimulation with high spatial resolution can be realized, which are beneficial for improving the fidelity of the transmission matrix for the transmission and scattering of the compensated expanded light in the multimode fiber 3 and the intracranial medium. In this way, after the multimode fiber 3 is implanted in a fixed position of the intracranial space of the experimental subject 4, not only can the light focusing with high spatial resolution be achieved at further position away from the output end 32, but also the technical effect of improving the focus depth of the optical stimulation, which is performed by the optogenetics experiment method using the wavefront shaping, is achieved.

In an embodiment of the present application, after the step of providing an optical stimulation, time sequence optical stimulation is further performed. The step of performing the time sequence optical stimulation comprises: performing time sequence variable wavefront compensation to the light to be input into the input end 31, according to a relation function between the spatial position of the optical stimulation and the time and the transmission matrix of the multimode fiber 3, to form a time sequence compensated expanded light; and inputting the time sequence compensated expanded light from the input end 31 into the multimode fiber 3, such that the time sequence compensated expanded light, after transmitted by the multimode fiber 3 to the output end 32 and output from the output end 32, is capable of dynamically focusing within the field of view of the output end 32 according to the relation function between the spatial position of the optical stimulation and the time. When performing optical stimulation on the intracranial cells in the experimental subject 4, by providing the compensated expanded light with time sequence characteristics, the compensated expanded light entering into the input end 31 varies over time according to the required relation between the spatial position and the time, thereby forming the time sequence compensated expanded light. The focus of the light output from the output end 32 varies over time, and is capable of achieving a series of continuous optical stimuli to the intracranial space of the experimental subject 4, such that the optical stimulation has temporal resolution, which is beneficial to the study of the neurological behavior of the experimental subject 4 under a series of time sequence variable stimuli.

It should be understood that the step of providing the optical stimulation itself can also be regarded as a portion of the time sequence optical stimulation, no matter the technical solution of one-time optical stimulation to the intracranial space of the experimental subject 4 or the technical solution of time sequence optical stimulation to the intracranial space of the experimental subject, both technical solutions are included within the protection scope of the present application.

Figure 4:
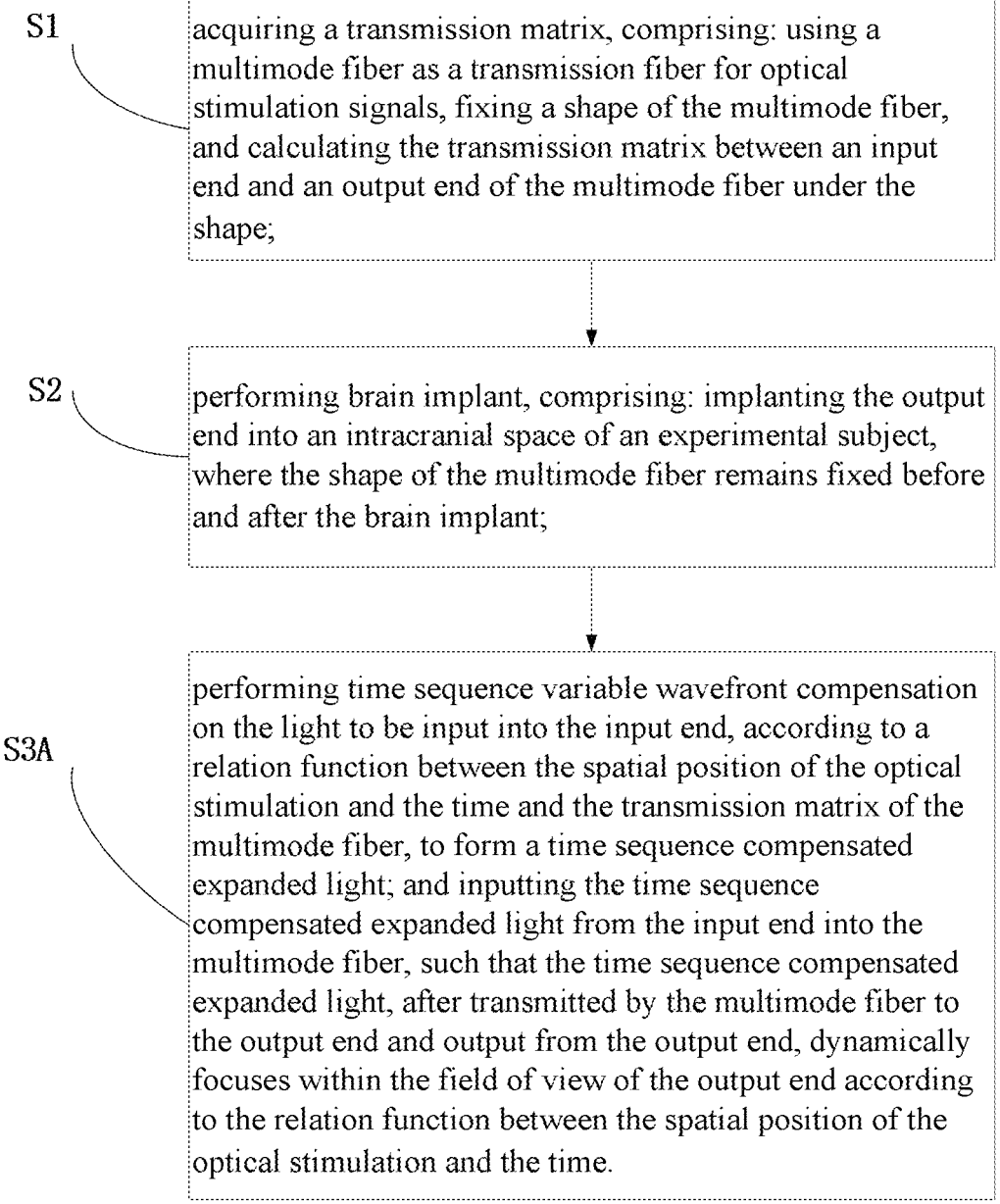
FIG. 4 is a flow chart of a temporally selective method for optogenetics experiments in accordance with an embodiment of the present application.

Referring to FIG. 4 and FIG. 5, as a specific technical solution of an embodiment of the present application, the method for optogenetics experiments may comprise the following steps:

S1: acquiring a transmission matrix, comprising: using a multimode fiber 3 as a transmission fiber for optical stimulation signals, fixing a shape of the multimode fiber 3, and calculating the transmission matrix between an input end 31 and an output end 32 of the multimode fiber 3 under the shape;

S2: performing brain implant, comprising: implanting the output end 32 into an intracranial space of an experimental subject 4, where the shape of the multimode fiber 3 remains fixed before and after the brain implant;

S3A: performing time sequence variable wavefront compensation to the light to be input into the input end 31, according to a relation function between the spatial position of the optical stimulation and the time and the transmission matrix of the multimode fiber 3, to form a time sequence compensated expanded light; and inputting the time sequence compensated expanded light from the input end 31 into the multimode fiber 3, such that the time sequence compensated expanded light, after transmitted by the multimode fiber 3 to the output end 32 and output from the output end 32, is capable of dynamically focusing within the field of view of the output end 32 according to the relation function between the spatial position of the optical stimulation and the time.

In an embodiment of the present application, in the step of performing time sequence variable wavefront compensation to the light to be input into the input end 31 of the multimode fiber 3 to form the time sequence compensated expanded light, a digital micromirror device 2 is adopted to perform spatial light modulation, where the compensated expanded light is output by the digital micromirror device 2, by continuously updating an output pattern of the digital micromirror device 2, the time sequence variable wavefront compensation is achieved and the time sequence compensated expanded light is formed. In the method for optogenetics experiments provided in this embodiment, the digital micromirror device is used as the spatial light modulator, which is capable of projecting the compensated expanded light after wavefront shaping into the input end 31 of the multimode fiber 3 with a sufficient high updating rate (updating every 50 microseconds), and realizing high-resolution focusing at the output end 32 with a sufficient large field of view. In this way, the dynamic light focusing is achieved in the intracranial space of the experimental subject 4, and the spatiotemporal resolution of the method for optogenetics experiments is improved.

In an embodiment of the present application, before said performing the bran implant, the method further comprises: transcribing a gene expressing light sensitive proteins into the intracranial space of the experimental subject 4. By transcribing a gene expressing light sensitive proteins into the intracranial space of the experimental subject 4, the ion channels on the cell membrane are opened or closed by the light sensitive proteins under the influence of light pulses, the membrane potential or calcium ion concentration of the neuronal cells is controlled to activate or inhibit the excitation of neuronal cells, such that the neuronal cells can respond to optical stimulation at corresponding wavelengths to achieve the regulation of neural function.

In an embodiment of the present application, the step of transcribing a gene expressing light sensitive proteins into the intracranial space of the experimental subject 4 comprises: injecting a retrovirus into the intracranial space of the experimental subject 4, in which, a gene of the retrovirus contains a gene segment capable of being expressed as the light sensitive proteins. The intracranial space of the experimental subject 4 is injected with a retrovirus carrying a gene segment capable of being expressed as the light sensitive proteins, which enables the experimental subject 4 to produce the light sensitive proteins during normal metabolism and therefore respond to the optical stimulation transmitted to the intracranial space via the multimode fiber 3.

It should be understood that the step of transcribing a gene expressing light sensitive proteins into the intracranial space of the experimental subject 4 and the step S1 of acquiring the transmission matrix can be performed in parallel without time sequence relation therebetween.

In one embodiment of the present application, after the step of brain implant, the multimode fiber 3 and the experimental subject 4 are fixed, so as to keep the shape and position of the multimode fiber 3 unchanged, as well as the position of the output end 32 of the multimode fiber 3 within the intracranial space of the experimental subject 4 unchanged. In this way, the transmission matrix of the multimode fiber 3 and the relationship between the compensated expanded light and the optical stimulation point are prevented from changing, and multiple times calculation of the transmission matrix of the multimode fiber are avoided.

An specific embodiment of a method for optogenetics experiments is provided hereinbelow.

An embodiment provides a method for optogenetics experiments based on wavefront shaping, and the method is performed as follows:

acquisition of the transmission matrix: a multimode fiber 3 is used as a transmission fiber for optical stimulation signals, and a shape of the multimode fiber 3 is fixed. Thereafter, a high speed camera is adopted to: collect a light intensity and a light phase information of the light field at the output end 32 of the multimode fiber 3 multiple times when a specific compensated expanded light is input into the input end 31 of the multimode fiber 3; or alternatively, collect a light intensity and a light phase information of the light field at the input end 31 of the multimode fiber 3 multiple times when a specific compensated expanded light is input into the output end 32 of the multimode fiber 3.

Thereafter, the transmission matrix of the multimode fiber 3 is calculated by using a transmission matrix solution algorithm according to the light distribution information collected multiple times.

Brain implant: the output end 32 is implanted into an intracranial space of an experimental subject 4, where the shape of the multimode fiber 3 remains fixed before and after the brain implant;

Before the brain implant, a retrovirus containing a gene segment capable of being expressed as the light sensitive proteins is injected into the intracranial space of the experimental subject 4, so as to perform transcription of the gene capable of being expressed as the light sensitive proteins into the intracranial space of the experimental subject 4. After the brain implant, the multimode fiber 3 and the experimental subject 4 are maintained fixed.

The time sequence optical stimulation is performed. According to a relation function between the spatial position of the optical stimulation and the time, the transmission matrix of the multimode fiber 3, and the optical environment of the intracranial space of the experimental subject 4, a digital micromirror device 2 is adopted to perform time sequence variable wavefront compensation to the light to be input into the input end 31 of the multimode fiber 3. By continuously updating an output pattern of the digital micromirror device, the time sequence compensated expanded light is formed. The time sequence compensated expanded light is input from the input end 31 into the multimode fiber 3, such that the time sequence compensated expanded light, after transmitted by the multimode fiber 3 to the output end 32 and output from the output end 32, is capable of realizing dynamical focus within the field of view of the output end 32 according to the relation function between the spatial position of the optical stimulation and the time.

In the method for optogenetics experiments provided in this embodiment, since the time sequence compensated expanded light after wavefront shaping is input into the input end 31 of the multimode fiber 3, a focusing light with extremely strong spatial and temporal precision is output at the output end 32 of the multimode fiber, such that a dynamic precise stimulation with a cell scale precision can be realized. Because the actual condition of the intracranial space of the experimental subject 4 is compensated, and the scattering field of the intracranial space is used as a part of the wavefront shaping compensation, a deeper stimulation depth is resulted and therefore optical stimulation at a position further away from the output end 32 of the multimode fiber 3 can be realized. By embedding the slender multimode fiber 3 into the cranium of the experimental subject 4 to perform experiments, the damage to the cranium of the experimental subject 4 is small, and the practical application value is high. In addition, because the multimode fiber 3 is always fixed, it is possible to achieve dynamic high-precision optical stimulation without measuring the transmission matrix multiple times.

It is another object of the present application to provide an experimental system using the above-mentioned method for optogenetics experiments. Referring to FIG. 5, the system includes: a laser 1, a digital micromirror device 2, a multimode fiber 3, and an experimental subject 4. The laser emitted by the laser 1 is performed with optical path adjustment to become an expanded light, which is performed with wavefront shaping by the digital micromirror device 2 to become a compensated expanded light. The compensated expanded light is coupled into the input end 31 of the multimode fiber 3, transmitted within the multimode fiber according to the transmission matrix, and the output end 32 extends into the intracranial space of the experimental subject 4, and the compensated expanded light converges within the field of view of the output end 32 and stimulates intracranial neurons of the experimental subject 4.

The above description is only optional embodiments of the present application and is not intended to limit the present application. Any modification, equivalent replacement, and improvement made within the spirit and principle of the present application shall be included within the protection scope of the present application.

What is claimed is:

1. A method for optogenetics experiments, based on wavefront shaping and comprising:
   acquiring a transmission matrix, comprising: using a multimode fiber as a transmission fiber for optical stimulation signals, fixing a shape of the multimode fiber, and calculating the transmission matrix between an input end and an output end of the multimode fiber under the shape;
   performing brain implant, comprising: implanting the output end into an intracranial space of an experimental subject, wherein the shape of the multimode fiber remains fixed before and after the brain implant; and
   providing an optical stimulation, comprising: enabling a spatial position of the optical stimulation to be within a field of view of the output end, performing wavefront compensation to a light to be input into the input end, according to the spatial position of the optical stimulation and the transmission matrix of the multimode fiber, to form a compensated expanded light, and inputting the compensated expanded light from the input end into the multimode fiber, such that the compensated expanded light, after being transmitted by the multimode fiber to the output end and output from the output end, is capable of focusing at the spatial position of the optical stimulation.

2. The method of claim 1, wherein in the step of acquiring a transmission matrix, said calculating the transmission matrix between an input end and an output end of the multimode fiber under the shape comprises:
   collecting a light distribution information of a light field at the output end of the multimode fiber multiple times when a specific compensated expanded light is input into the input end of the multimode fiber; or alternatively, collecting a light distribution information of a light field at the input end of the multimode fiber multiple times when a specific compensated expanded light is input into the output end of the multimode fiber; and
   calculating the transmission matrix of the multimode fiber by using a transmission matrix solution algorithm according to the light distribution information collected at the light field at the output end of the multimode fiber or the light field at the input end of the multiple fiber multiple times.

3. The method of claim 2, wherein the light distribution information of the light field comprises: a light intensity and a light phase information of the light field.

4. The method of claim 1, wherein in the step of providing an optical stimulation, the compensated expanded light is modified according to an optical environment of the intracranial space of the experimental subject, and the compensated expanded light is capable of focusing at a predetermined spatial coordinate after the output end of the multimode fiber is implanted into the intracranial space of the experimental subject.

5. The method of claim 1, further comprising, after the step of providing an optical stimulation, performing time sequence optical stimulation.

6. The method of claim 5, wherein the step of performing time sequence optical stimulation comprises:

performing time sequence variable wavefront compensation to the light to be input into the input end, according to a relation function between the spatial position of the optical stimulation and the time and the transmission matrix of the multimode fiber, to form a time sequence compensated expanded light; and inputting the time sequence compensated expanded light from the input end into the multimode fiber, such that the time sequence compensated expanded light, after transmitted by the multimode fiber to the output end and output from the output end, is capable of dynamically focusing within the field of view of the output end according to the relation function between the spatial position of the optical stimulation and the time.

7. The method of claim 6, wherein in the step of performing time sequence variable wavefront compensation to the light to be input into the input end of the multimode fiber to form the time sequence compensated expanded light, a digital micromirror device is adopted to perform spatial light modulation, wherein the compensated expanded light is output by the digital micromirror device, by continuously updating an output pattern of the digital micromirror device, the time sequence variable wavefront compensation is achieved and the time sequence compensated expanded light is formed.

8. The method of claim 1, further comprising, before said performing the brain implant, transcribing a gene expressing light sensitive proteins into the intracranial space of the experimental subject.

9. The method of claim 8, wherein the step of transcribing a gene expressing light sensitive proteins into the intracranial space of the experimental subject comprises: injecting a retrovirus into the intracranial space of the experimental subject, wherein a gene of the retrovirus contains a gene segment capable of being expressed as the light sensitive proteins.

10. A system for optogenetics experiments, adopting the method according to claim 1.

* * * * *